United States Patent [19]
Stilwell et al.

[11] Patent Number: 5,484,913
[45] Date of Patent: Jan. 16, 1996

[54] CALCIUM-MODIFIED OXIDIZED CELLULOSE HEMOSTAT

[75] Inventors: Reginald L. Stilwell; Elaine J. Whitmore, both of Arlington, Tex.; Lowell G. Saferstein, Edison, N.J.

[73] Assignee: Johnson & Johnson Medical, Inc., Arlington, Tex.

[21] Appl. No.: 410,246

[22] Filed: Mar. 24, 1995

Related U.S. Application Data

[63] Continuation-in-part of Ser. No. 173,325, Dec. 23, 1993, abandoned.

[51] Int. Cl.$^6$ .......................................................... C08B 1/02
[52] U.S. Cl. ............................. 536/57; 536/76; 536/127; 525/54.2; 424/443; 424/444; 424/446; 424/447; 602/900; 604/292; 604/213
[58] Field of Search ............................... 536/57, 76, 127; 525/54.2; 424/443, 444, 446, 447; 604/292; 606/213; 602/900

[56] References Cited

U.S. PATENT DOCUMENTS

| | | | |
|---|---|---|---|
| 2,517,772 | 8/1950 | Doub et al. . | |
| 3,666,750 | 5/1972 | Briskin et al. | 424/180 |
| 4,655,211 | 4/1987 | Sakamoto et al. | 128/156 |
| 5,134,229 | 7/1992 | Saferstein et al. | 536/56 |

FOREIGN PATENT DOCUMENTS

| | | |
|---|---|---|
| 1593513 | 7/1981 | United Kingdom . |

*Primary Examiner*—Nathan M. Nutter
*Attorney, Agent, or Firm*—Andrew C. Farmer

[57] ABSTRACT

A calcium-modified oxidized cellulose hemostat provides faster hemostasis than does either unmodified or sodium- or potassium-modified oxidized cellulose. The percentage by weight of calcium in the modified oxidized cellulose must be in a range between about 0.5 and about 4, in order to enhance hemostasis, while not interfering excessively with bioabsorbability. In a second embodiment, an oxidized cellulose hemostat is modified with both calcium and either sodium or potassium. The second embodiment may be used to deliver acid-sensitive materials.

17 Claims, No Drawings

CALCIUM-MODIFIED OXIDIZED CELLULOSE HEMOSTAT

This is a continuation-in-part of application Ser. No. 08/173,325, filed Dec. 23, 1993 and now abandoned.

BACKGROUND OF THE INVENTION

1. Field of the Invention

This invention relates to a process for preparing a bioresorbable hemostat by treating oxidized cellulose with calcium or a combination of calcium and sodium or potassium.

2. Description of the Related Art

Oxidized cellulose fabrics are bioresorbable and absorbent fabrics that have long been used in medical applications. Both naturally-occurring and regenerated cellulose can be oxidized. For convenience and brevity, we refer to both as "oxidized cellulose." Three examples of such a fabric are Interceed* (TC7) Absorbable Adhesion Barrier, Surgicel* Absorbable Hemostat and Surgicel Nu-Knit* Absorbable Hemostat (all available from Johnson & Johnson Medical, Inc., Arlington, Tex.). However, all these materials are acidic. The pH of the aqueous phase of 1 g of Interceed Barrier suspended in 100 ml of purified water is approximately 4.1. The surface pH of a fully water-saturated piece of fabric is about 1.7. Materials such as thrombin, tissue plasminogen activator analogue (t-PAA), and other highly acid-sensitive materials are inactivated immediately on such matrices, precluding their use for delivery of these materials to a surgical site. Alternatively, if such a material is to be delivered on an oxidized cellulose fabric, the fabric must first be neutralized. Thus, past efforts to modify oxidized cellulose in order to improve its properties have generally focused on neutralizing the material.

Doub et al., in U.S. Pat. No. 2,517,772, describe the impregnation of neutralized oxidized cellulose products with thrombin. They disclose a method of neutralizing oxidized cellulose cloth with an aqueous sodium bicarbonate solution (Example 2) or an aqueous calcium acetate solution (Example 1). Example 2 of the Doub et al. patent discloses neutralizing oxidized cellulose gauze with an aqueous solution of strongly basic sodium bicarbonate and then impregnating the neutralized product with thrombin. The thrombin impregnated gauze is then frozen and dried from the frozen state to provide a highly hemostatic surgical dressing. The patent does not disclose any practical data pertaining to testing in animals.

Dol'berg et al., *Farm Zh.* (Kiev) 1971,26(2),53–56, studied the hemostatic properties of oxidized cellulose and combined the material with various pharmaceutical compounds. They report that the sodium and potassium salts of oxidized cellulose can be used in medicine and that the potassium salt has advantages over the acid form, in that it is neutral and is compatible with many pharmaceutical substances.

Barinka et al., in British Patent Specification 1,593,513, published Jul. 15, 1981, disclose a process for oxidizing cellulose with a mixture of nitric acid and stabilized ("phlegmatized") sodium nitrate. The material is then stabilized with an aqueous-alcoholic solution of urea or its N, N-disubstituted alkyl or acyl derivatives. Finally, the oxidized cellulose is converted to its calcium, sodium, or ammonium salt by repeatedly alternating absorption-in and centrifuging-off a solution of an equimolar mixture of chloride and acetate of calcium, sodium, or ammonium.

Saferstein et al., in U.S. Pat. No. 5,134,229, disclose a process for preparing storage stable oxidized cellulose by contacting an acidic oxidized cellulose material with a water and alcohol solution of a slightly basic salt of a weak acid to elevate the pH of the cellulose material to between 5 and 8. Their salt of a weak acid is preferably selected from among sodium acetate, potassium acetate, sodium citrate, sodium formate, potassium citrate, potassium formate, disodium hydrogen phosphate, dipotassium hydrogen phosphate, or mixtures thereof. Repeating the processes of Doub et al., they found that neutralizing oxidized cellulose cloth in aqueous solutions of sodium bicarbonate results in a cloth that is partially gelled, distorted from its original size, and very weak, with little integrity. The tensile strength of the cloth is too low for practical use such as, for example, a hemostat. Completely neutralizing oxidized cellulose cloth with calcium acetate in accordance with the teachings of Example 1 of the Doub et al. patent, they found, provides a cloth that is of acceptable integrity but is irritating to mammalian skin and other body cells at the point of contact. Further, large, whitish masses presumed to be granuloma tissue forms at the application site of the cloth. Apparently, such tissue is attempting to encapsulate the calcium salt of the oxidized cellulose cloth. Saferstein et al. do not disclose a calcium salt as an option for neutralizing oxidized cellulose.

The role of calcium in hemostasis is well known; in fact, the International Committee on Nomenclature of Blood Clotting Factors has designated calcium as one of 13 blood-coagulation factors (Factor IV). Calcium plays an important role in the conversion of protothrombin to thrombin, one of the stages of the blood coagulation process. Details of the hemostasis process appear in standard medical texts, such as *Remington's Pharmaceutical Sciences,* ed. by A. R. Gennaro (Mack, Easton, Pa., 1990). There are also examples of the practical application of calcium to enhance hemostasis. Superstat* absorbable collagen hemostat contains calcium ions to enhance its hemostatic efficacy. On the other hand, to prevent blood from coagulating inadvertently, citric acid is added to blood collection bags to sequester the calcium in blood serum.

Despite the recognized value of neutralized oxidized cellulose as a hemostatic material and the important role that calcium plays in hemostasis, the goal of an absorbable calcium-modified hemostat had not been realized before the present invention.

SUMMARY OF THE INVENTION

In accordance with the present invention, a process for preparing a bioabsorbable surgical hemostat comprises the steps of:

(a) contacting an oxidized cellulose material that contains a predetermined concentration of carboxylic acid with a chloride-free solution of a calcium salt of a weak acid to neutralize about 5.5% to about 45% of the carboxylic acid and (b) washing the material to remove excess salt.

In this specification and the appended claims, unless specified otherwise, percentages are understood to be weight percent.

The hemostat that results from the process of this invention is an oxidized cellulose fabric that comprises between 0.5% and 4% calcium, preferably between about 2.0% and about 3.5%. The fabric evidences greater hemostatic activity than does either unmodified oxidized cellulose or oxidized cellulose that has been neutralized with sodium or potassium salts. Hemostat whose calcium concentration is less than 3.5% does not irritate the skin and other body cells as does fabric containing a higher concentration.

In another embodiment of this invention, a process for preparing a bioabsorbable surgical hemostat comprises the steps of:

(a) contacting an oxidized cellulose material that contains a predetermined concentration of carboxylic acid with a chloride-free solution of a calcium salt of a weak acid and a sodium or potassium salt of a weak acid to neutralize about 50% to about 80% of the carboxylic acid, the salt concentrations selected so that the calcium neutralizes about 5.5% to about 45% of the acid and the sodium or potassium salt neutralizes the balance, and (b) washing the material to remove excess salt.

DETAILED DESCRIPTION OF THE INVENTION

The present invention provides an oxidized cellulose surgical hemostat that demonstrates greater hemostatic activity than either acidic or neutralized oxidized cellulose of the prior art. By using substantially less calcium than was used with material of the prior art, the present process yields material that shows faster bioabsorption and greater biocompatibility than oxidized cellulose that is neutralized with (greater amounts of) calcium.

The process by which the hemostat of the present invention is prepared is somewhat similar to the process described in U.S. Pat. No. 5,134,229 ('229), incorporated herein by reference. The differences include the amount and composition of the basic salt that is used to modify the composition of the hemostatic material. In one embodiment, the material is treated with a calcium salt, rather than the sodium and potassium salts disclosed in '229. In another embodiment, the composition is modified by addition of combined Ca and Na- or K-salts. In both cases, the salts are chloride-free to avoid forming hydrochloric acid, which can cause oxidized cellulose to decompose into low molecular weight polymer, with loss of tensile strength and shortened shelf life. Weak acid does substantially no damage.

Preferably, the calcium salt is calcium acetate, which is water and alcohol soluble, but other salts are suitable, as well, such as citrate, formate, butyrate, and propionate.

After the material is modified, it is washed to remove excess salt. Water, alcohol, and other organic solvents well known in the art, as well as mixtures, are suitable for washing. Organic solvents are preferred because they facilitate subsequent drying of the material. Water is less preferred, because the material has a tendency to shrink as it dries if it is not stretched while drying.

Typically, carboxylic acid groups comprise about 18% to 21% by weight of the oxidized cellulose starting material and calcium attaches to and neutralizes the carboxylic acid groups. The amount of calcium salt determines the degree of neutralization, and an amount that neutralizes about 5.5% to 45% of the acid groups is preferred. The calcium enhances the hemostatic properties of the material. If too much calcium is used, however, the fabric causes irritation. The preferred calcium concentration is about 2.0% to about 3.5% by weight.

It is sometimes desirable to have more-fully neutralized material. For example, if acid-sensitive moieties are to be added to the material, then higher pH is desirable. For fabric to be used with thrombin, for example, pH should be in the range from about 5.0 to about 8.0, preferably in the range from about 6.5–7.0. The pH is measured as follows: A 1 g sample of material is placed in a 150 ml beaker, to which is added 100 ml of recently boiled and cooled purified water. The sample is stirred and allowed to stand for 5 minutes, after which the liquid is decanted into a clean dry beaker and the pH of the liquid is measured. Sodium or potassium salt is preferably used to provide higher neutralization, without yielding fabric that causes irritation. Suitable salts include sodium acetate, sodium citrate, sodium formate, disodium hydrogen phosphate, potassium acetate, potassium citrate, potassium formate, dipotassium hydrogen phosphate, and mixtures thereof. The preferred concentration of sodium or potassium in fabric that is more-fully neutralized is in the range from about 2% to about 6%.

The preferred process for preparing neutralized oxidized cellulose of the present invention is to first contact an acidic oxidized cellulose fabric with a calcium salt solution whose amount and molarity is selected to provide 5.5% to 45% neutralization of the carboxylic acid groups. To prepare more-fully neutralized material, an amount and molarity of sodium and/or potassium salt is used which, together with the calcium salt, will preferably provide about 50% to 80% neutralization. Although solutions in either water or alcohol can be used, mixtures of water and alcohol are preferred.

When an acid-sensitive medicament is added to the fabric, the addition is typically accomplished by dipping the fabric into a saline solution of the medicament to saturate the fabric. Suitable medicaments include thrombin, fibrinogen, and antifibrinolytics such as Aprotinin. Thrombin is a preferred addition to provide enhanced hemostasis. Thrombin solutions of 1000 U/ml of saline are commercially available and are suitable.

EXAMPLES

The following examples demonstrate the processes and products of this invention. The examples are not to be interpreted as limiting the scope of the invention, but rather as contributing to a complete description of the invention.

Example 1

Preparation of Calcium-modified Nu-Knit* Containing 0.5% by Weight Calcium 50 grams of Surgicel Nu-Knit* cloth with a 20% carboxylic acid content (0.22 moles of carboxylic acid) was slit to a 30.5 cm width, wrapped around a plastic perforated core, and placed in a canister. 1600 ml of isopropyl alcohol (IPA) (1257.6 grams) and 1600 ml of distilled water (1600 grams) were added to a Haake model FS circulating bath. The circulating bath was connected to the canister so that the solution flowed into the bottom of the canister and up the perforated core, percolating through the plies of cloth wrapped around the core.

1.07 grams of calcium acetate monohydrate (0.006 moles) were dissolved in 25 ml of distilled water: 25 ml of IPA. This was added all at once to the circulating bath as the solution circulated around the cloth. The concentration of the calcium acetate monohydrate in the solution (w/w) of water: IPA was 1.07/2902.25×100=0.0368%. The reaction was stopped after 2 hours of circulating the solution.

The core was removed from the canister and placed in a cylinder with 800 ml of IPA. This was stirred for 30 minutes, the solvent was removed and replaced with fresh isopropyl alcohol and stirred for 30 minutes. The fabric was removed and air dried in a laboratory hood. The sample of fabric was analyzed for calcium by atomic absorption and found to have 0.45% by weight calcium. Titration of the fabric for carbolic acid content showed the fabric had a carboxyl content of 18.9%, indicating a 5.5% degree of neutralization.

Example 2

Preparation of Calcium-modified Surgicel* Containing about 0.8% by Weight Calcium 48.6 grams of Surgicel* with a 20% carboxylic acid content (0.216 moles of carboxylic acid) was slit into a 10 cm width, wrapped around a 30.5 cm long perforated core, and placed in a canister. The canister was attached to a Haake model FS circulating bath. Into the bath was added 1850 ml of IPA (1454.1 grams) and 1850 ml (1850 grams) of distilled water. The solvent was circulated around the cloth for a few minutes.

1.90 grams of calcium acetate monohydrate (0.010 moles) was dissolved in 40 ml of IPA and 40 ml of distilled water. This solution was added to a dropping funnel and slowly added to the Haake circulating bath over a ½ hour period. The solution was then allowed to circulate for 2 hours around the fabric. The concentration of the calcium acetate monohydrate wt/wt (wt. of calcium acetate/wt. of solvent) in solution was 1.9/3375.5×100=0.056%. After 2 hours the cloth was removed from the canister and placed in a graduated cylinder with 100% IPA. The IPA solution was stirred around the cloth for 30 minutes to remove water; then the solvent was replaced with fresh IPA and stirred around the cloth for another 30 minutes. The cloth was hung in a hood to air dry. The concentration of calcium measured by atomic absorption was found to be 0.79% by weight. Titration of the cloth for carboxylic acid content showed an 18% carboxylic content or a 10% degree of neutralization.

Example 3

Preparation of Calcium-modified Surgicel* with 2.3% Calcium 49.4 grams of Surgicel with a 20% carboxylic acid content (0.219 moles of carboxylic acid) was slit to a 10 cm width, wrapped around a plastic mandrel, and placed in a canister. 1850 ml of distilled water (1850 grams) and 1850 ml of IPA (1454.1 grams) were added to the circulating bath and circulated around the canister and the fabric for 5 minutes.

5.80 grams of calcium acetate monohydrate (0.033 moles) was dissolved in 100 ml of isopropyl alcohol/100 ml distilled water. This was added to a dropping funnel and slowly dripped into the circulating solvent over a 30 minute period. The concentration of the calcium acetate wt/wt in the solution was 0.166% (5.8/3482.7×100). This solution was allowed to circulate for 2 hours around the cloth; then the core was removed from the canister.

The core was placed in a 1-liter cylinder and filled with 800 ml of 100% IPA. This solution was stirred with a magnetic stir bar around the core for 30 minutes to remove water from the cloth. The solvent was removed and replaced with 800 ml of fresh IPA and stirred for 30 more minutes. The cloth was then hung in a hood to air dry. Analysis of the fabric for calcium showed 2.3% by weight calcium. Titration showed a 14.6% carboxylic acid content or a 27% degree of neutralization.

The degree of neutralization indicates the weight percent of the original carboxylic acid groups that have been converted to the calcium salt. The remaining carboxylic acid groups have not been changed and therefore exist as free acids.

Examples 4–8

Preparation of Calcium-modified Surgical* and Surgicel Nu-Knit* Having Various Percentages of Calcium The procedure of Examples 1–3 was followed, except that calcium acetate concentration was varied to provide calcium-modified Nu-Knit* with 0.8%, 2.3% and 5.5% calcium and Surgicel* with 0.5% and 5.5% calcium. The hemostasis efficacies of all eight samples and of unmodified control samples were measured using the swine splenic incision model. Results appear in Table 1.

TABLE 1

| | Hemostasis Study of Nu-Knit* and Calcium-Modified Nu-Knit* | | | | |
|---|---|---|---|---|---|
| | NU-KNIT Control | NU-KNIT with 0.5% Calcium | NU-KNIT with 0.8% Calcium | NU-KNIT with 2.3% Calcium | NU-KNIT with 5.5% Calcium |
| Bleeding Time in Minutes | 9.0 | 5.0 | 4.5 | 3.50 | 3.25 |
| | 7.0 | 4.5 | 5.0 | 3.25 | 3.00 |
| | 5.0 | 5.0 | 4.0 | 3.50 | 3.25 |
| | 6.0 | 4.5 | 4.5 | 4.00 | 3.50 |
| | 6.5 | 5.0 | 5.0 | 4.50 | 3.00 |
| | 6.5 | 5.5 | 5.0 | 3.50 | 3.00 |
| Average | 6.6 | 4.9 | 4.6 | 3.7 | 3.1 |

TABLE 1-continued

Hemostasis Study of Surgicel* and Calcium-Modified Surgicel*

|  | SURGICEL Control | SURGICEL with 0.5% Calcium | SURGICEL with 0.8% Calcium | SURGICEL with 2.3% Calcium | SURGICEL with 5.5% Calcium |
| --- | --- | --- | --- | --- | --- |
| Bleeding | 14.0 | 12.0 | 11.0 | 8.25 | 6.0 |
| Time in | 11.0 | 11.5 | 10.5 | 9.25 | 6.5 |
| Minutes | 11.0 | 12.0 | 11.5 | 9.75 | 5.25 |
|  | 12.5 | 10.5 | 10.0 | 8.0 | 6.5 |
|  | 13.0 | 11.0 | 9.5 | 8.5 | 6.0 |
|  | 14.0 | 10.5 | 10.0 | 8.5 | 7.0 |
| Average | 12.5 | 11.25 | 10.4 | 8.7 | 6.2 |

Example 9

"Excessive" Calcium Modification of ORC

Example 6 of U.S. Pat. No. 2,517,772 (Doub et al.) was repeated to make a calcium-neutralized oxidized cellulose cloth. This cloth was analyzed for calcium content by atomic absorption and found to contain 6.75% calcium.

Oxidized cellulose cloth made by the present invention, which contained 2.77% calcium as measured by atomic absorption, and the cloth made by following Example 6 of Doub et al., containing 6.75% calcium, were implanted in the subcutaneous tissue of rats and were evaluated for absorbability and tissue acceptability 14 days post operative. The calcium ORC of this invention evoked only a very mild degree of tissue reaction customarily seen with Surgicel*. The material was completely absorbed in most animals, and only a small amount of soft, gelatinous material was found in a few animals. The calcium ORC made by Example 6 of Doub et al. consistently evoked severe reactions in the form of large moderately firm, whitish, non-fibrous masses presumed to be granulation tissue and capsule formation. In addition, implants were not completely absorbed after 14 days.

Analysis of the examples recited by Barinka et al. (Brit. Pat. Spec. 1,593,513) shows that they form calcium-modified ORC having properties similar to that of Doub et al.

Example 10

Calcium- Versus Sodium-modification of ORC

Hemostasis efficacy of calcium-modified Surgicel* and Nu-Knit* were measured against similarly modified sodium-Surgicel and sodium-Nu-Knit. All fabrics were similarly neutralized to comparable degrees. The Surgicel and Nu-Knit fabrics were modified by treatment with calcium acetate to neutralize about 30% of the carboxylic acid groups on the oxidized cellulose fabrics. This produced a cloth with a 2.6% calcium content. Neutralization of Surgicel and Nu-Knit with sodium acetate produced a cloth with a 2.9% sodium content, which corresponds to about 30% degree of neutralization.

The hemostasis efficacy was measured using the swine splenic incision model. Table II shows the results of the hemostasis test. Results are the average of 5 bleeding events.

TABLE II

| Test Materials | Hemostasis Time |
| --- | --- |
| Surgicel | 8.0 min. |
| Nu-Knit | 5.0 min. |
| Calcium Surgicel | 5.5 min. |
| Calcium Nu-Knit | 3.3 min. |
| Sodium Surgicel | 6.5 min. |
| Sodium Nu-Knit | 4.5 min. |

The tests indicate that both sodium- and calcium-modified oxidized cellulose fabrics are faster hemostats than the corresponding parent material; however, the calcium-modified oxidized cellulose fabrics are faster than the comparably neutralized sodium fabrics. This can be attributed to the role calcium plays in hemostasis.

Example 11

A Mixed Calcium/Sodium Oxidized Cellulose Cloth

Into a resin kettle that contained 170 ml IPA and 170 ml of distilled water were added 0.984 grams of calcium acetate hydrate and 1.52 grams of sodium acetate trihydrate. The contents were stirred until both salts were dissolved. The salts were present in molar quantity each to neutralize 30% of the carboxylic acid groups on the oxidized cellulose. 8.4 grams of Surgicel cloth, with a carboxylic acid content of 20%, were added to this solution, and the solution was stirred for 4 hours. The cloth was then removed and washed with two 1650 ml portions of IPA. The cloth was dried in air. The pH of the cloth in distilled water, measured as described earlier, was 5.58. Analysis of the cloth for calcium and sodium by atomic absorption showed 2.03% calcium and 2.2% sodium. The pH of the cloth was higher than if calcium alone were used. (A similar cloth modified only with 30% stoichiometric calcium acetate showed a pH in distilled water of 4.1) In this example, the fabric's pH was raised sufficiently so that it was compatible with acid sensitive medicament and yet had sufficient calcium for enhanced hemostasis, without exceeding the 3.5% concentration above which calcium produces tissue irritation.

We claim:

1. A bioabsorbable surgical hemostat comprising a neutralized oxidized cellulose fabric comprising between about 0.5% and about 4.0% calcium.

2. The surgical hemostat of claim 1 in which the fabric comprises between about 2.0% and about 3.5% calcium.

3. The surgical hemostat of claim 1, further comprising about 2% to about 6% sodium or potassium.

4. The surgical hemostat of claim 3, further comprising a hemostatic-effective amount of thrombin.

5. A process for preparing a bioabsorbable surgical hemostat comprising the steps of:
   (a) contacting an oxidized cellulose material that contains a predetermined concentration of carboxylic acid with a sufficient quantity of a chloride-free solution of a calcium salt of a weak acid to neutralize about 5.5% to about 45% of the carboxylic acid and provide a calcium content in the fabric of between about 0.5% and about 4.0%; and
   (b) washing the material to remove excess salt.

6. A process for preparing a bioabsorbable surgical hemostat comprising the steps of:
   (a) contacting an oxidized cellulose material that contains a predetermined concentration of carboxylic acid with a sufficient quantity of a chloride-free solution of a calcium salt of a weak acid and a quantity of a sodium or potassium salt of a weak acid to neutralize about 50% to about 80% of the carboxylic acid, with the calcium neutralizing about 5.5% to about 45% of the acid the sodium or potassium salt neutralizing the balance, and providing a calcium content in the fabric of between about 0.5% and about 4.0%; and
   (b) washing the material to remove excess salt.

7. The process of claim 6 including the additional step of impregnating the dried material with a hemostatic-effective amount of thrombin.

8. The surgical hemostat of claim 3 wherein the fabric comprises between about 2% and 3.5% calcium.

9. The surgical hemostat of claim 8 wherein the fabric has a pH between 5.0 and 8.0.

10. The surgical hemostat of claim 9 wherein the fabric has a pH between 6.5 and 7.0.

11. The surgical hemostat of claim 10, further comprising a hemostatic-effective amount of thrombin.

12. The process according to claim 5 wherein the quantitiy and molarity of the calcium salt of a weak acid is determined prior to the step of contacting it with the oxidized cellulose material.

13. The process according to claim 5 wherein the calcium salt of a weak acid comprises calcium acetate monohydrate.

14. The process according to claim 5 wherein the calcium salt of a weak acid is added in a quantity to provide a calcium content in the fabric of between 2% and 3.5%.

15. The process according to claim 6 and further comprising the step of impregnating the material with a therapuetically effective amount of an acid sensitive therapuetic agent.

16. The process of claim 15 wherein the therapuetic agent is selected from the group comprising: thrombin, tissue plasminogen activator analogue, fibrinogen or an antifibrinolytic.

17. The process of claim 16 wherein the therapeutic agent comprises thrombin.

* * * * *